United States Patent
Kim

(10) Patent No.: US 10,610,155 B2
(45) Date of Patent: Apr. 7, 2020

(54) SPECTRUM ACQUISITION APPARATUS AND METHOD

(71) Applicant: SAMSUNG ELECTRONICS CO., LTD., Suwon-si (KR)

(72) Inventor: Sangkyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 601 days.

(21) Appl. No.: 15/391,019

(22) Filed: Dec. 27, 2016

(65) Prior Publication Data

US 2018/0020970 A1 Jan. 25, 2018

(30) Foreign Application Priority Data

Jul. 21, 2016 (KR) ........................ 10-2016-0092792

(51) Int. Cl.
*A61B 5/00* (2006.01)

(52) U.S. Cl.
CPC ............ *A61B 5/489* (2013.01); *A61B 5/0075* (2013.01); *A61B 5/0077* (2013.01); *A61B 5/441* (2013.01); *A61B 5/6841* (2013.01); *A61B 5/7246* (2013.01); *A61B 5/742* (2013.01); *A61B 5/7405* (2013.01); *A61B 5/7455* (2013.01); *A61B 5/002* (2013.01)

(58) Field of Classification Search
CPC ......... A61B 5/00; A61B 5/0075; A61B 5/742; A61B 5/7405; A61B 5/7246; A61B 5/489; A61B 5/441; A61B 5/0077; A61B 5/6841; A61B 5/7455; A61B 5/002

See application file for complete search history.

(56) References Cited

U.S. PATENT DOCUMENTS

| | | | |
|---|---|---|---|
| 6,016,435 | A | 1/2000 | Maruo et al. |
| 8,244,334 | B2 | 8/2012 | Huang et al. |
| 8,295,904 | B2 | 10/2012 | Goldman et al. |
| 8,660,318 | B2 | 2/2014 | Komura et al. |
| 9,095,285 | B2 | 8/2015 | Ryabov et al. |
| 9,289,160 | B2 | 3/2016 | Ryabov et al. |
| 2014/0159862 | A1 | 6/2014 | Yang et al. |
| 2014/0236019 | A1 | 8/2014 | Rahum |
| 2014/0316269 | A1 | 10/2014 | Zhang et al. |
| 2015/0216484 | A1* | 8/2015 | Kasahara ............. A61B 5/1118 600/301 |

FOREIGN PATENT DOCUMENTS

| | | |
|---|---|---|
| JP | 2006-102110 A | 4/2006 |
| KR | 10-2014-0092486 A | 7/2014 |
| KR | 10-2016-0001263 A | 1/2016 |

* cited by examiner

*Primary Examiner* — Eric J Messersmith

(74) *Attorney, Agent, or Firm* — Sughrue Mion, PLLC

(57) ABSTRACT

Provided are an apparatus and method for acquiring a spectrum based on a vein pattern. The spectrum acquisition apparatus may include a spectroscope configured to emit light onto a user's skin and receive light reflected or scattered from the skin, a vein pattern recognizer configured to recognize a vein pattern of a body area at which the spectroscope is located, and a spectroscope controller configured to control the spectroscope based on a vein pattern recognition result to acquire a skin spectrum of a body area of interest.

17 Claims, 6 Drawing Sheets

SPECTRUM ACQUISITION APPARATUS AND METHOD

CROSS-REFERENCE TO RELATED APPLICATION

This application claims priority from Korean Patent Application No. 10-2016-0092792, filed on Jul. 21, 2016, in the Korean Intellectual Property Office, the disclosure of which is incorporated herein in its entirety by reference.

BACKGROUND

1. Field

Apparatuses and methods consistent with exemplary embodiments relate to a spectrum measurement technology, and more particularly, to an apparatus and method for acquiring a spectrum based on a vein pattern.

2. Description of Related Art

Diabetes is one of the modern chronic diseases, which is diagnosed when an insulin hormone is not properly secreted from a pancreas, and glucose within blood is not transferred to cells for use as energy and is accumulated in the blood. Diabetes may lead to complications, such as high blood pressure, renal failure, blindness, and the like.

Blood glucose measurement methods may include an invasive method that measures a blood glucose level from a blood sample directly collected from a patient, and a non-invasive method that measures a blood glucose level without drawing blood. The invasive method shows high measurement reliability, while causing pain, inconvenience and a high risk of infection due to use of an injector. Also, the invasive method can incur an economic burden to the patients due to use of consumables, such as strips for measuring body fluid components, disposal syringes, and the like. In the non-invasive method, a variety of optical technologies such as Raman spectroscopy, near infrared spectroscopy, and mid-infrared spectroscopy have been applied.

Meanwhile, in the non-invasive method associated with optical technology, even a slight change in a spectroscope's spectral measurement location may lead to an increase in spectral measurement noise. The increase in spectral measurement noise is a cause of lower measurement reliability of the non-invasive method using optical technology.

SUMMARY

Exemplary embodiments overcome the above problems and/or disadvantages and other disadvantages not described above. Also, the exemplary embodiments are not required to overcome the disadvantages described above, and may not overcome any of the problems described above.

One or more exemplary embodiments may provide an apparatus and method for acquiring a spectrum of a body area of interest based on a vein pattern.

According to an aspect of an exemplary embodiment, there is provided a spectrum acquisition apparatus including: a spectroscope configured to emit light onto a user's skin and receive light reflected or scattered from the skin, a vein pattern recognizer configured to recognize a vein pattern of a body area at which the spectroscope is located, and a spectroscope controller configured to control the spectroscope based on a vein pattern recognition result to acquire a skin spectrum of a body area of interest.

The vein pattern recognizer may emit infrared light to the body area at which the spectroscope is located and recognize the vein pattern by receiving infrared light reflected or scattered from the body area.

The spectroscope controller may compare the vein pattern recognition result with a stored vein pattern and determine whether the spectroscope is located at the body of area of interest based on a comparison result.

The spectroscope controller may operate the spectroscope only when the spectroscope is located at the body area of interest so that the skin spectrum of the body area of interest is acquired.

The spectroscope controller may select a skin spectrum, which is measured when the spectroscope is located at the body area of interest from among a plurality of skin spectra measured by the spectroscope, and acquire the skin spectrum of the body area of interest.

The spectroscope controller may adjust a location of the spectroscope in response to determining that the spectroscope is not located at the body area of interest.

The spectrum acquisition apparatus may be equipped in a wearable device.

According to an aspect of another exemplary embodiment, there is provided a spectrum acquisition apparatus including: a spectroscope configured to emit light onto a user's skin and receive light reflected or scattered from the skin, a vein pattern recognizer configured to recognize a vein pattern of a body area at which the spectroscope is located, a processor configured to generate guideline information for moving the spectroscope to a body area of interest based on a vein pattern recognition result, and an outputter configured to output the guideline information.

The vein pattern recognizer may emit infrared light to the body area at which the spectroscope is located and recognize the vein pattern by receiving infrared light reflected or scattered from the body area.

The processor may determine a relative position of the spectroscope with respect to the body area of interest by comparing the vein pattern recognition result with a stored vein pattern.

The guideline information may include information about a moving direction and a moving distance for moving the spectroscope from a current location to the body area of interest.

The outputter may output the guideline information through at least one of audible, visual, and tactile manners.

The spectrum acquisition apparatus may be equipped in a wearable device.

According to an aspect of another exemplary embodiment, there is provided a spectrum acquisition method including: recognizing a vein pattern of a body area at which a spectroscope is located, and acquiring a skin spectrum of a body area of interest based on a vein pattern recognition result.

The recognizing of the vein pattern may include emitting infrared light to the body area at which the spectroscope is located and recognizing the vein pattern by receiving infrared light reflected or scattered from the body area.

The acquiring of the skin spectrum of the body area of interest may include comparing the vein pattern recognition result with a stored vein pattern and determining whether the spectroscope is located at the body area of interest based on a comparison result.

The acquiring of the skin spectrum of the body area of interest may further include operating the spectroscope only when the spectroscope is located at the body area of interest so that the skin spectrum of the body area of interest is acquired.

The acquiring of the skin spectrum of the body area of interest may further include selecting a skin spectrum, which is measured when the spectroscope is located at the body area of interest from among a plurality of skin spectra measured by the spectroscope, and acquiring the skin spectrum of the body area of interest.

The acquiring of the skin spectrum of the body area of interest may further include adjusting a location of the spectroscope in response to determining that the spectroscope is not located at the body area of interest.

DETAILED DESCRIPTION

Figure 1:
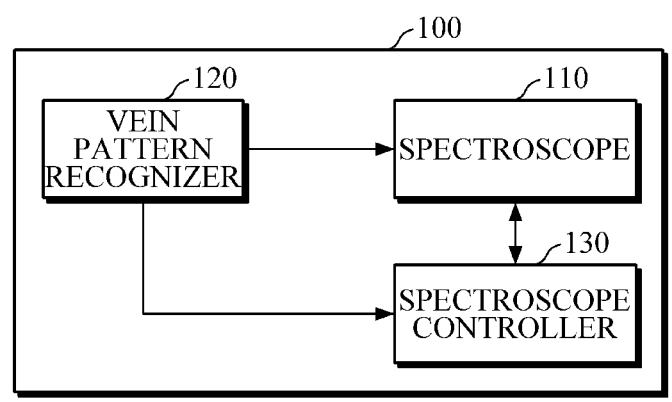
FIG. 1 is a block diagram illustrating an exemplary embodiment of a spectrum acquisition apparatus.

Exemplary embodiments will be described in detail with reference to the accompanying drawings. In the following description, like drawing reference numerals are used for like elements, even in different drawings. The relative size and depiction of these elements may be exaggerated for clarity, illustration, and convenience. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail. The terms used herein are defined in consideration of the functions of the exemplary embodiments and may be changed depending on a user, the intent of an operator, or a custom. Accordingly, the terms should be defined based on the description throughout the specification.

Expressions such as "at least one of," when preceding a list of elements, modify the entire list of elements and do not modify the individual elements of the list.

As is traditional in the field of the inventive concepts, embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

FIG. 1 is a block diagram illustrating an exemplary embodiment of a spectrum acquisition apparatus. The spectrum acquisition apparatus 100 may be an apparatus that recognizes a vein pattern and acquires a skin spectrum of a desired area of a human body based on a result of the vein pattern recognition.

The spectrum acquisition apparatus 100 may be realized as a software module or manufactured in the form of a hardware chip to be equipped in an electronic device. In this case, the electronic device may include a mobile phone, a smartphone, a tablet computer, a laptop computer, a personal digital assistant (PDA), a portable multimedia player (PMP), a navigation system, a MP3 player, a digital camera, and a wearable device. The wearable device may include devices of a wristwatch type, a wristband type, a ring-type, a belt-type, a necklace type, an ankle band type, a thigh band type, a forearm band type, etc. However, the electronic device and the wearable device are not limited thereto.

Referring to FIG. 1, the spectrum acquisition apparatus 100 may include a spectroscope 110, a vein pattern recognizer 120, and a spectroscope controller 130.

The spectroscope 110 may emit light onto a user's skin, receive light reflected or scattered from the skin, and measure the skin spectrum through spectroscopy of the received light. The spectroscope 110 may include a light source, such as a light emitting diode (LED), a laser diode, etc., and a light detector such as a photodiode, a phototransistor (PTr), a charged coupled device (CCD), etc.

The vein pattern recognizer 120 may recognize a vein pattern of a body area in which the spectroscope 110 is located. For example, the vein pattern recognizer 120 may emit infrared light to the body area in which the spectroscope 110 is located, and recognize a vein pattern of the body area by receiving infrared light reflected or scattered from the body area. Because hemoglobin contained in the blood absorbs infrared light by its nature, the vein pattern recognizer 120 may recognize the veins of an object using such properties of hemoglobin.

The spectroscope controller 130 may control the operation of the spectroscope 110 based on the vein pattern recognition result, and acquire a skin spectrum of a body area of interest. For example, the spectroscope controller 130 may compare the vein pattern recognition result with a stored vein pattern of the body area of interest in order to determine whether the spectroscope 110 is located at the body area of interest, and control the operation of the spectroscope 110 based on the determination so that the skin spectrum of the body area of interest can be acquired.

According to one exemplary embodiment, the spectroscope controller 130 may operate the spectroscope 110 only when the spectroscope 110 is located at a body area of interest, so as to acquire the skin spectrum of the body area. In other words, when the spectroscope 110 is not located at the body area of interest, the spectroscope controller 130 does not activate the spectroscope 110, but activates the spectroscope 110 only when the spectroscope 110 is located at the desired body area, thereby preventing unnecessary power consumption.

According to another exemplary embodiment, in order to obtain the skin spectrum of the body area of interest, the spectroscope controller 130 may select a skin spectrum that is measured when the spectroscope 110 is located at the body area of interest from among a plurality of skin spectra measured by the spectroscope 110.

According to another exemplary embodiment, when the spectroscope 110 is not located at the body area of interest, the spectroscope controller 130 may automatically adjust the location of the spectroscope 110, and operate the spectroscope 110 automatically or according to a user's command so as to acquire the skin spectrum of the body area of interest.

Figure 2:
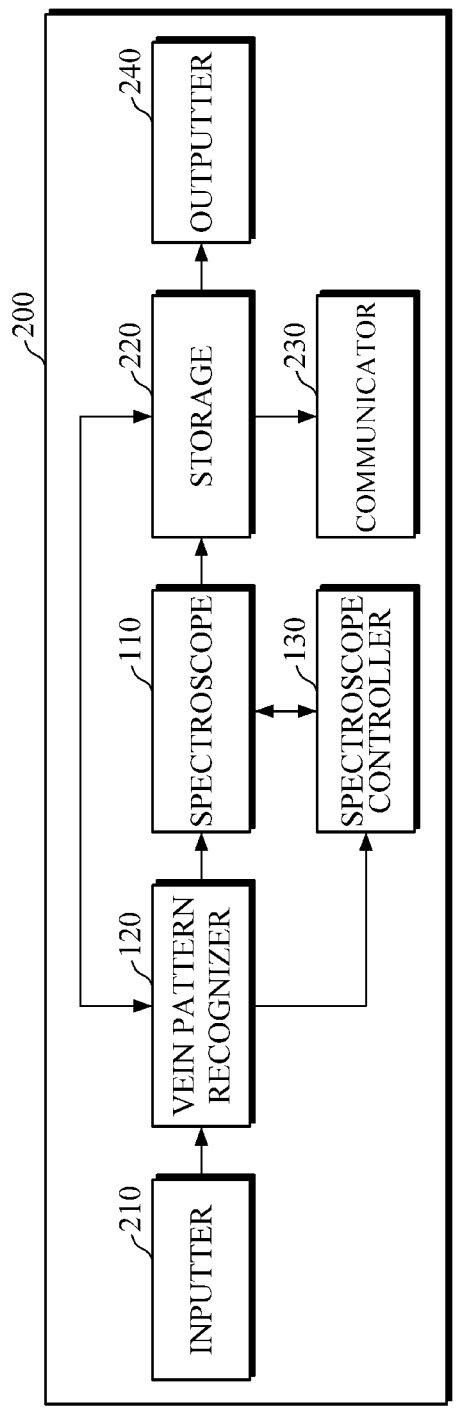
FIG. 2 is a block diagram illustrating another exemplary embodiment of the spectrum acquisition apparatus.

FIG. 2 is a block diagram illustrating another exemplary embodiment of the spectrum acquisition apparatus.

Referring to FIGS. 1 and 2, the spectrum acquisition apparatus 200 of FIG. 2 may optionally further include an inputter 210, a storage 220, a communicator 230, and an outputter 240, as compared with the spectrum acquisition apparatus 100 of FIG. 1. A spectroscope 110, a vein pattern recognizer 120, and a spectroscope controller 130 are the same as those of the apparatus 100 described with reference to FIG. 1, and thus detailed descriptions thereof will be omitted.

The inputter 210 may receive various control signals from a user. According to one exemplary embodiment, the inputter 210 may include a key pad, a dome switch, a touch pad (static pressure or capacitive), a jog wheel, a jog switch, a hardware button, and the like. For example, when a touch pad and a display form a mutual layer structure, this can be referred to as a touch screen.

The storage 220 may store programs or commands for operating the spectrum acquisition apparatus 200 and store input/output data. In addition, the storage 220 may store vein pattern data of a body area of interest.

The storage 220 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the spectrum acquisition apparatus 200 may operate an external storage medium, such as web storage, which performs the storage function of the storage 220.

The communicator 230 may communicate with an external device. For example, the communicator 230 may transmit data input by a user though the inputter 210, vein pattern recognition result data of the vein pattern recognizer 120, and skin spectrum data measured by the spectroscope 110 to the external device, or receive a variety of data useful for acquiring a skin spectrum of the body area of interest from the external device.

In this case, the external device may be a medical device that uses the measured skin spectrum, a printer for printing a result, or a display device that displays the vein pattern recognition result information or the skin spectrum information. In addition, the external device may be a digital TV, a desktop computer, a mobile phone, a smartphone, a tablet PC, a notebook computer, a PDA, a PMP, a navigation system, an MP3 player, a digital camera, a wearable device, or the like, but the examples thereof are not limited thereto.

The communicator 230 may communicate with the external device through various types of communication protocols, such as Bluetooth, Bluetooth low energy (BLE), near-field communication (NFC), wireless local area network (WLAN), ZigBee, infrared data association (IrDA), Wi-Fi direct (WFD), ultra-wideband (UWB), Ant+, Wi-Fi, radio frequency identification (RFID), etc. However, the above-described communication protocols are merely examples and the communication protocols are not limited thereto.

The outputter 240 may output the vein pattern recognition result data, the measured skin spectrum data, and so on. According to one exemplary embodiment, the outputter 240 may output the vein pattern recognition result data, the measured skin spectrum data, and other data through at least one of audible, visual and tactile manners. For example, the outputter 240 may output the vein pattern recognition result data, the measured skin spectrum data, and other data using audio, text, and vibration. The outputter 240 may include a display, a speaker, a vibrator, or the like.

Figure 3:
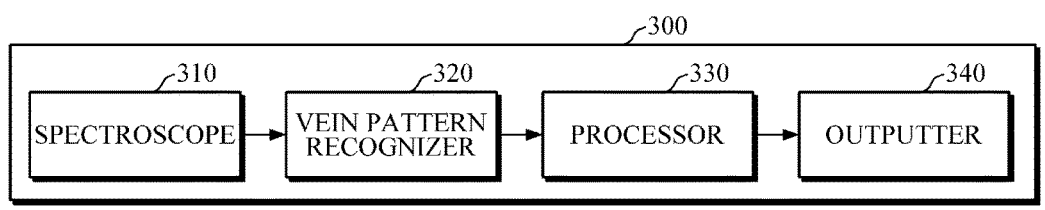
FIG. 3 is a block diagram illustrating another exemplary embodiment of the spectrum acquisition apparatus.

FIG. 3 is a block diagram illustrating another exemplary embodiment of the spectrum acquisition apparatus.

Referring to FIG. 3, the spectrum acquisition apparatus 300 may include a spectroscope 310, a vein pattern recognizer 320, a processor 330, and an outputter 340.

The spectroscope 310 may emit light to the user's skin, receive light reflected or scattered from the user's skin, and measure a skin spectrum through spectroscopy of the received light. The spectroscope 310 may include a light source, such as an LED, a laser diode, etc., and a light detector such as a photodiode, a phototransistor (PTr), a CCD, etc.

The vein pattern recognizer 320 may recognize a vein pattern of a body area at which the spectroscope 310 is located. For example, the vein pattern recognizer 320 may emit infrared light to the body area in which the spectroscope 310 is located, and recognize the vein pattern of the body area by receiving infrared light reflected or scattered from the body area.

The processor 330 may generate guideline information based on the vein pattern recognition result such that the spectroscope 310 moves to a body area of interest. Here, the guideline information may include information about a moving direction and a moving distance of the spectroscope 310 such that the spectroscope 310 moves from the current position to the body area of interest.

According to one exemplary embodiment, the processor 330 may compare the vein pattern recognition result with a stored vein pattern of the body area of interest, determine the relative position of the spectroscope 310 with respect to the body area of interest, and generate the guideline information for moving the spectroscope 310 from the current location to the body area of interest.

The outputter 340 may output the generated guideline information. According to one exemplary embodiment, the outputter 340 may output the generated guideline information through at least one of audible, visual, and tactile manners. For example, the outputter 340 may output guideline information that is generated using audio, text, and vibration. The outputter 340 may include a display, a speaker, a vibrator, etc.

Figure 4:
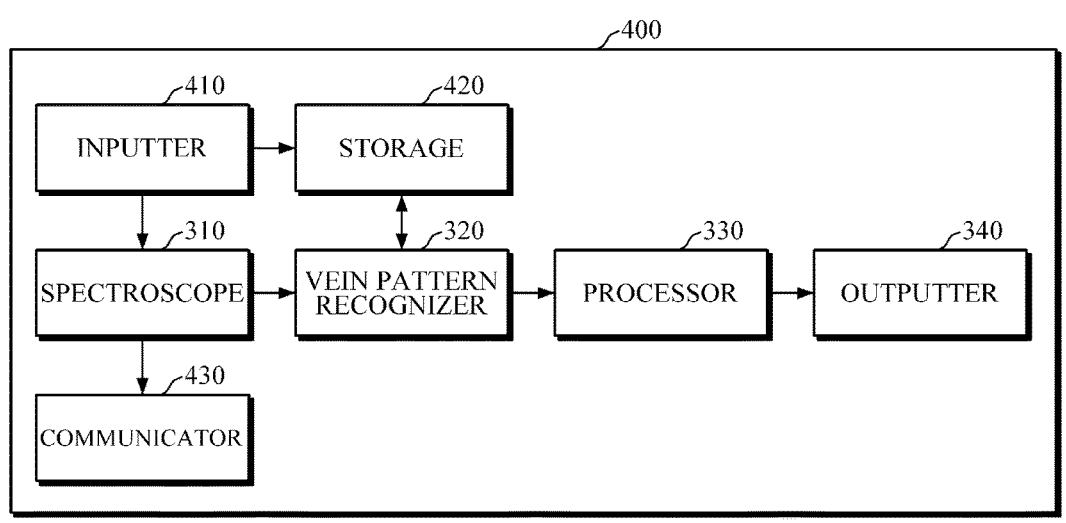
FIG. 4 is a block diagram illustrating another exemplary embodiment of the spectrum acquisition apparatus.

FIG. 4 is a block diagram illustrating another exemplary embodiment of the spectrum acquisition apparatus.

Referring to FIGS. 3 and 4, the spectrum acquisition apparatus 400 of FIG. 4 may optionally further include an inputter 410, a storage 420, and a communicator 430, as compared with the spectrum acquisition apparatus of FIG. 3. A spectroscope 310, a vein pattern recognizer 320, a processor 330, and an outputter 340 are the same as those described with reference to FIG. 3, and thus detailed descriptions thereof will be omitted.

The inputter 410 may receive various control signals from a user. According to one exemplary embodiment, the inputter 410 may include a key pad, a dome switch, a touch pad (static pressure or capacitive), a jog wheel, a jog switch, a hardware button, and the like. For example, when a touch pad and a display form a mutual layer structure, this can be referred to as a touch screen.

The storage 420 may store programs or commands for operating the spectrum acquisition apparatus 400 and store input/output data. In addition, the storage 420 may store vein pattern data of a body area of interest.

The storage 420 may include a flash memory, a hard disk, a micro type multimedia card, and a card type memory (e.g., SD or XD memory), a RAM, an SRAM, a ROM, an EEPROM, a PROM, a magnetic memory, a magnetic disk, an optical disk, and the like. In addition, the spectrum acquisition apparatus 400 may operate an external storage medium, such as web storage, which performs the storage function of the storage 420.

The communicator 430 may communicate with an external device. For example, the communicator 430 may transmit data input by a user through the inputter 410, vein pattern recognition result data of the vein pattern recognizer 320, skin spectrum data measured by the spectroscope 310, and the guideline information generated by the processor 330 to the external device, or receive a variety of data useful for acquiring the skin spectrum of the body area of interest from the external device.

In this case, the external device may be a medical device that uses the measured skin spectrum, a printer for printing a result, or a display device that displays the vein pattern recognition result information or the skin spectrum information. In addition, the external device may be a digital TV, a desktop computer, a mobile phone, a smartphone, a tablet PC, a notebook computer, a PDA, a PMP, a navigation system, an MP3 player, a digital camera, a wearable device, or the like, but the examples thereof are not limited thereto.

The communicator 430 may communicate with the external device through various types of communication protocols, such as Bluetooth, BLE, NFC, WLAN, ZigBee, IrDA, WFD, UWB, Ant+, Wi-Fi, RFID, etc. However, the above-described communication protocols are merely examples and the communication protocols are not limited thereto.

Figure 5:
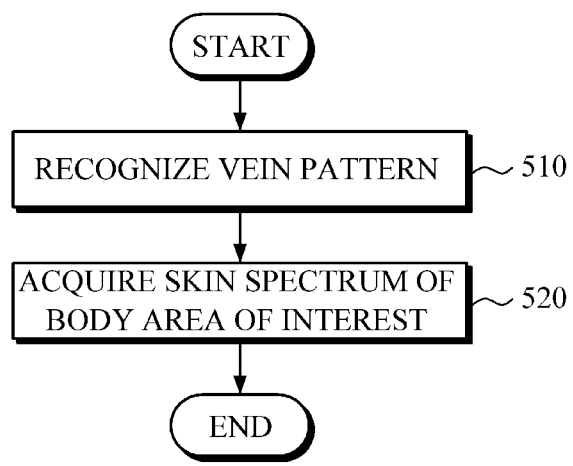
FIG. 5 is a flowchart illustrating an exemplary embodiment of a spectrum acquisition method.

FIG. 5 is a flowchart illustrating an exemplary embodiment of a spectrum acquisition method.

Referring to FIGS. 1 and 5, the spectrum acquisition apparatus 100 recognizes a vein pattern of a body area at which the spectroscope 110 is located (operation 510). For example, the spectrum acquisition apparatus 100 may emit infrared light to the body area at which the spectroscope 110 is located, receive light reflected or scattered from the body area, and recognize the vein pattern of the body area.

The spectrum acquisition apparatus 100 obtains a skin spectrum of a body area of interest based on the vein pattern recognition result (operation 520). For example, the spectrum acquisition apparatus 100 may compare the vein pattern recognition result with a stored vein pattern of the body area of interest in order to determine whether the spectroscope 110 is located at the body area of interest, and control the spectroscope 110 based on the determination so that the skin spectrum of the body area of interest can be acquired.

According to one exemplary embodiment, the spectrum acquisition apparatus 100 may operate the spectroscope 110 only when the spectroscope 110 is located at a body area of interest, so as to acquire the skin spectrum of the body area. In other words, when the spectroscope 110 is not located at the body area of interest, the spectrum acquisition apparatus 100 does not activate the spectroscope 110, but activates the spectroscope 110 only when the spectroscope 110 is located at the desired body area, thereby preventing unnecessary power consumption.

According to another exemplary embodiment, the spectrum acquisition apparatus 100 may select a skin spectrum that is measured when the spectroscope 110 is located at the body area of interest from among a plurality of skin spectra measured by the spectroscope 110.

According to another exemplary embodiment, when the spectroscope 110 is not located at the body area of interest, the spectrum acquisition apparatus 100 may automatically adjust the location of the spectroscope 110, and operate the spectroscope 110 automatically or according to a user's command so as to acquire the skin spectrum of the body area of interest.

Figure 6:
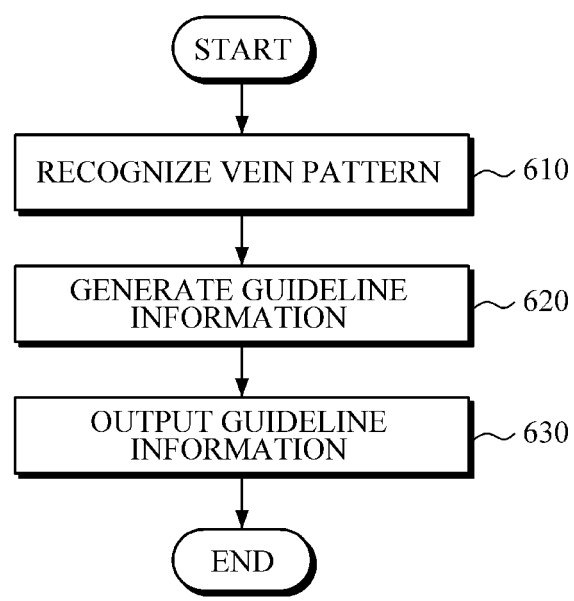
FIG. 6 is a flowchart illustrating another exemplary embodiment of the spectrum acquisition method.

FIG. 6 is a flowchart illustrating another exemplary embodiment of the spectrum acquisition method.

Referring to FIGS. 3 and 6, the spectrum acquisition apparatus 300 may recognize a vein pattern of a body area at which the spectroscope 310 is located (operation 610). For example, the spectrum acquisition apparatus 300 may emit infrared light to the body area where the spectroscope 110 is located, and recognize a vein pattern of the body area by receiving infrared light reflected or scattered from the body area.

The spectrum acquisition apparatus 300 may generate guideline information based on the vein pattern recognition result such that the spectroscope 310 moves to a body area of interest (operation 620). Here, the guideline information may include information about a moving direction and a moving distance of the spectroscope 310 such that the spectroscope 310 moves from the current position to the body area of interest.

According to one exemplary embodiment, the spectrum acquisition apparatus 300 may compare the vein pattern recognition result with a stored vein pattern of the body area of interest, determine the relative position of the spectroscope 310 with respect to the body area of interest, and generate the guideline information for moving the spectroscope 310 from the current location to the body area of interest.

The spectrum acquisition apparatus 300 may output the generated guideline information (operation 630). According to one exemplary embodiment, the spectrum acquisition apparatus 300 may output the generated guideline information through at least one of audible, visual, and tactile manners.

While not restricted thereto, the operations or steps of the methods or algorithms according to the above exemplary embodiments may be implemented as computer readable codes on a computer readable recording medium. Codes and code segments constituting the computer program can be easily inferred by a skilled computer programmer in the art. The computer readable recording medium includes all types of recording media in which computer readable data are stored. Examples of the computer readable recording medium include a ROM, a RAM, a CD-ROM, a magnetic tape, a floppy disk, and an optical disk. Further, the record medium may be implemented in the form of a carrier wave such as Internet transmission. In addition, the computer readable recording medium may be distributed to computer systems over a network, in which computer readable codes may be stored and executed in a distributed manner. Also, the operations or steps of the methods or algorithms according to the above an exemplary embodiments may be written as a computer program transmitted over a computer-readable transmission medium, such as a carrier wave, and received and implemented in general-use or special-purpose digital computers that execute the programs. Moreover, it is understood that in exemplary embodiments, one or more units (e.g., those represented by a block as illustrated in FIGS. 1 through 4) of the above-described apparatuses and devices can include or implemented by circuitry, a processor, a microprocessor, etc., and may execute a computer program stored in a computer-readable medium.

While one or more exemplary embodiments have been described with reference to the figures, it should be understood by those skilled in the art that various modifications in form and details may be made therein without departing from the sprit and scope as defined by the appended claims. Therefore the description of the exemplary embodiments should be construed in a descriptive sense only and not to limit the scope of the claims, and many alternatives, modifications, and variations will be apparent to those skilled in the art.

What is claimed is:

1. A spectrum acquisition apparatus comprising:
a spectroscope configured to emit light onto a skin of a user and receive light reflected or scattered from the skin;
a vein pattern recognizer configured to recognize a vein pattern of a body area at which the spectroscope is located; and
a spectroscope controller configured to control the spectroscope based on a vein pattern recognition result to acquire a skin spectrum of a body area of interest,
wherein the spectroscope controller is further configured to:
compare the vein pattern recognition result with a stored vein pattern and determine whether the spectroscope is located at the body area of interest based on a comparison result, and
control the spectroscope to operate to acquire the skin spectrum of the body area based on a determination that the spectroscope is located at the body area of interest, and control the spectroscope not to operate to acquire the skin spectrum of the body area based on a determination that the spectroscope is not located at the body area of interest.

2. The spectrum acquisition apparatus of claim 1, wherein the vein pattern recognizer is configured to emit infrared light to the body area at which the spectroscope is located and recognize the vein pattern by receiving infrared light reflected or scattered from the body area.

3. The spectrum acquisition apparatus of claim 1, wherein the spectroscope controller is configured to operate the spectroscope only in response to determining that the spectroscope is located at the body area of interest so that the skin spectrum of the body area of interest is acquired.

4. The spectrum acquisition apparatus of claim 1, wherein the spectroscope controller is configured to select a skin spectrum, which is measured in response to determining that the spectroscope is located at the body area of interest from among a plurality of skin spectra measured by the spectroscope, and acquire the skin spectrum of the body area of interest.

5. The spectrum acquisition apparatus of claim 1, wherein the spectroscope controller is configured to adjust a location of the spectroscope in response to determining that the spectroscope is not located at the body area of interest.

6. The spectrum acquisition apparatus of claim 1 being equipped in a wearable device.

7. A spectrum acquisition apparatus comprising:
a spectroscope configured to emit light onto a skin of a user and receive light reflected or scattered from the skin;
a vein pattern recognizer configured to recognize a vein pattern of a body area at which the spectroscope is located;
a processor configured to generate guideline information for moving the spectroscope to a body area of interest based on a vein pattern recognition result; and
an outputter configured to output the guideline information.

8. The spectrum acquisition apparatus of claim 7, wherein the vein pattern recognizer is configured to emit infrared light to the body area at which the spectroscope is located and recognize the vein pattern by receiving infrared light reflected or scattered from the body area.

9. The spectrum acquisition apparatus of claim 7, wherein the processor is configured to determine a relative position of the spectroscope with respect to the body area of interest by comparing the vein pattern recognition result with a stored vein pattern.

10. The spectrum acquisition apparatus of claim 7, wherein the guideline information comprises information about a moving direction and a moving distance for moving the spectroscope from a current location to the body area of interest.

11. The spectrum acquisition apparatus of claim 7, wherein the outputter is configured to output the guideline information through at least one of audible, visual, and tactile manners.

12. The spectrum acquisition apparatus of claim 7 being equipped in a wearable device.

13. A spectrum acquisition method comprising:
recognizing a vein pattern of a body area at which a spectroscope is located; and
acquiring a skin spectrum of a body area of interest based on a vein pattern recognition result,
wherein the acquiring comprises comparing the vein pattern recognition result with a stored vein pattern and determining whether the spectroscope is located at the body area of interest based on a comparison result, and
wherein the acquiring the skin spectrum of the body area of interest comprises controlling the spectroscope to operate to acquire the skin spectrum of the body area based on a determination that the spectroscope is located at the body area of interest, and controlling the spectroscope not to operate to acquire the skin spectrum of the body area based on a determination that the spectroscope is not located at the body area of interest.

14. The spectrum acquisition method of claim 13, wherein the recognizing of the vein pattern comprises emitting infrared light to the body area at which the spectroscope is located and recognizing the vein pattern by receiving infrared light reflected or scattered from the body area.

15. The spectrum acquisition method of claim 13, wherein the acquiring of the skin spectrum of the body area of interest further comprises operating the spectroscope only in response to determining that the spectroscope is located at the body area of interest so that the skin spectrum of the body area of interest is acquired.

16. The spectrum acquisition method of claim 13, wherein the acquiring of the skin spectrum of the body area of interest further comprises selecting a skin spectrum, which is measured in response to determining that the spectroscope is located at the body area of interest from among a plurality of skin spectra measured by the spectroscope, and acquiring the skin spectrum of the body area of interest.

17. The spectrum acquisition method of claim 13, wherein the acquiring of the skin spectrum of the body area of interest further comprises adjusting a location of the spectroscope in response to determining that the spectroscope is not located at the body area of interest.

* * * * *